United States Patent [19]
Gertzman et al.

[11] Patent Number: 6,099,529
[45] Date of Patent: Aug. 8, 2000

[54] ALLOGRAFT BONE FIXATION SCREW METHOD AND APPARATUS

[75] Inventors: Arthur A. Gertzman, Stony Point, N.Y.; Timothy G. Haines, Minneapolis, Minn.

[73] Assignee: Musculoskeletal Transplant Foundation, Edison, N.J.

[21] Appl. No.: 09/275,024

[22] Filed: Mar. 24, 1999

Related U.S. Application Data

[63] Continuation-in-part of application No. 09/178,684, Oct. 26, 1998.

[51] Int. Cl.⁷ .................................................. A61B 17/56

[52] U.S. Cl. ............................................. 606/73; 606/72

[58] Field of Search ............................... 606/73, 232, 72; 411/310, 500, 501, 502, 503, 504, 505, 506, 507, 508, 509, 510, 399, 401, 409; 81/124.2

[56] References Cited

U.S. PATENT DOCUMENTS

| | | | |
|---|---|---|---|
| 4,724,731 | 2/1988 | Onofrio | 81/124.2 |
| 5,012,624 | 5/1991 | Dahlgren | 81/124.2 |

*Primary Examiner*—Michael Buiz
*Assistant Examiner*—(Jackie) Tan-Uyen T. Ho
*Attorney, Agent, or Firm*—John S. Hale; Gipple & Hale

[57] ABSTRACT

A bone screw assembly constructed of allograft bone comprising a screw shank with a uniform diameter threaded portion, an unthreaded portion with a outwardly tapered end terminating in a drive head defining a wedge shaped configuration to form an undercut for the drive head.

In operation a bore is drilled in the two bone sections, with one bone section being over drilled with the top portion of the over drilled bore having a tapered geometry which widens from the diameter of the bore. The bone screw is driven into the previously cut bore in the bone sections until the tapered surface of the bore engages the tapered undercut surface of the screw.

23 Claims, 4 Drawing Sheets

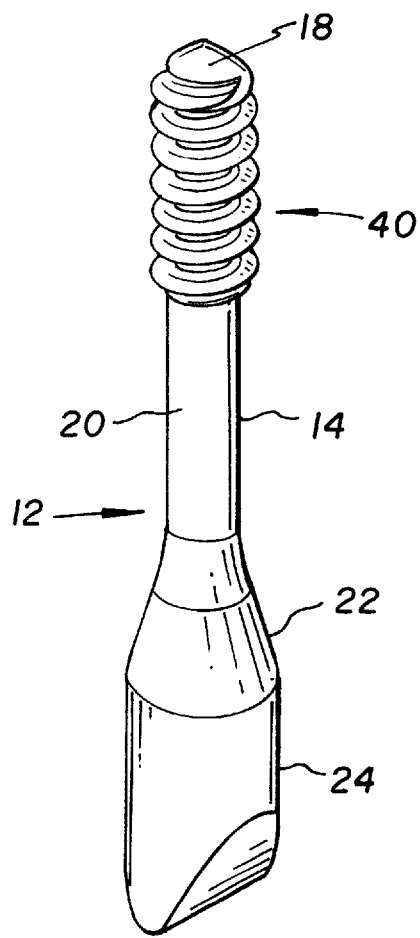
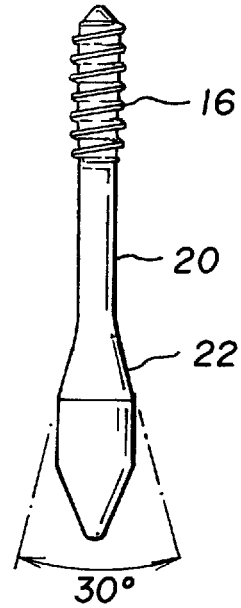
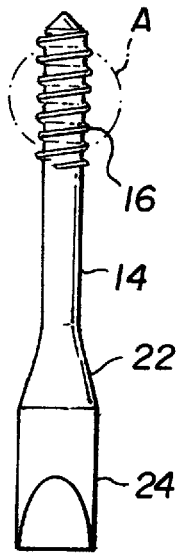
Fig. 1
Fig. 2
Fig. 3
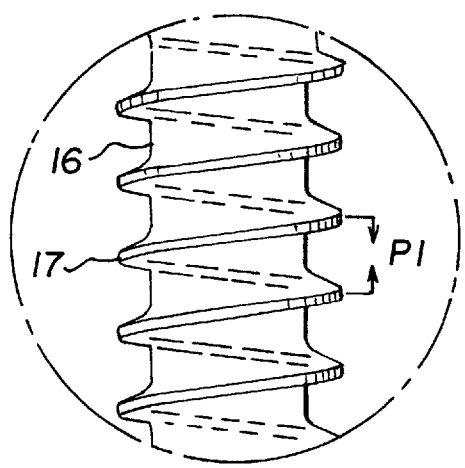
Fig. 4

ALLOGRAFT BONE FIXATION SCREW METHOD AND APPARATUS

RELATED APPLICATIONS

This application is a continuation-in-part of application Ser. No. 09/178,684, filed Oct. 26, 1998.

BACKGROUND OF THE INVENTION

1. Field of Invention

The present invention generally relates to threaded devices used to facilitate bone fracture or osteotomy fixation in human surgery and more specifically relates to threaded devices made of allograft bone.

2. Description of the Prior Art

The prior art contains many references directed to fastener drivers which drive screws having a Phillips head, standard slot head or other heads having various shaped slots or recesses which receive the torque from the driver end. See for example the prior art shown in U.S. Pat. No. 5,367,926. There are other examples of prior art fastener drivers having female driver ends which receive and drive fasteners having a male torque receiving end. Typical driver screw fasteners and screws of such a construction are shown in U.S. Pat. Nos. 755,804; 1,300,275; 4,724,731; 5,012,624; 5,443,482 and 5,730,744. Wrenches having a female driving end which drive caps or nuts are shown by U.S. Pat. Nos. 1,336,794 and 4,823,650.

Several patents such as U.S. Pat. Nos. 172,351 and 173,356 show screws having a head formed with a wedge shaped groove or slot which receives the angular notch of a driver head to transmit torque and drive the screw. While most screws have a uniform diameter shank, U.S. Pat. Nos. 4,463,753 and 5,403,136 disclose bone screws which have a tapered shank which cause compression of the bone between the distal end of the screw and the taper.

Millions of people suffer from a variety of musculoskeletal disorders or traumatic occurrences necessitating the use of devices to reduce osteotomies or fractures. Many different means have been developed to facilitate fixation and healing of the traumatized bone tissue. In the past, metallic pins and screws have been used to establish initial mechanical stability of the trauma site, and to facilitate permanent, mechanically stabile fracture or osteotomy healing.

The most significant difficulties with screws and pins currently used to facilitate fixation include the residual presence of "hardware" that may migrate, include adverse tissue reaction to the presence of foreign particulate debris, and otherwise compromise the functionality of the fixation. Some recently offered products feature bioresorbable material technology which allows for gradual absorption of the screws and pins. Unfortunately, these materials may fall short of expected performance due to incomplete osseointegration of patient bone. Allograft bone offers a suitably strong, biocompatible, and bioresorbable material that addresses these deficiencies.

Screws made completely of allograft bone have been described in F. Albee, *Bone Graft Surgery in Disease, Injury and Deformity* p. 22 (1940); and F. Albee, *The Improved Albee Bone Mill*, American Journal of Surgery p. 657 (March 1938). These screws offer the advantage of the biointegration of allograft bone tissue. However, the conventional slotted or rectangular head designs commonly used in metal screws when used with allograft bone screws, result in premature failure of the screws during intraoperative insertion due to excessively high shear forces applied to the head and the transition between the head and threaded portion of the screw. This shearing is due to several factors. First, and foremost, while bone is quite strong in compressive loading, it is relatively weak in tension and shear. Since the torque applied to a screw induces shear stresses, the design of a screw made of allograft bone tissue must be as robust as necessary with respect to torque loading.

SUMMARY OF THE INVENTION

In response to the needs still left unresolved by the prior art devices, the present invention contemplates allograft bone screws made of cortical and cancellous bone with both a unique head design and a bone formation treatment which solves the deficiencies of the prior art prostheses.

The inventive screw design offers two unique features which fulfill the potential of allograft bone as an ideal material for screws used in fracture and osteotomy reduction. The first unique feature is the wedge shaped drive head which mates with a specialized driver used to apply torque to the screw. This wedge shape accomplishes two desirable functions. The first function is that it avoids localized tensile stresses inherent in standard drive designs that would lead to mechanical failure of an allograft bone screw and the second function is the ability of this screw head geometry to act as a torque limiting means that also avoids mechanical failure of the screw. The second unique feature is an outwardly tapering shank portion adjacent the wedge shaped head which provides an undercut for the head providing a tight engagement of the screw in the bone bore.

Thus the present screw design is both easy to use and offers the ideal physiological response of patient tissue to allograft bone tissue.

In another aspect of the invention, a method is provided for implanting a bone screw into two separate bone sections. The approach includes the steps of drilling a first tapped bore drill through both pieces of bone. The first bone piece bore is then overdrilled to a larger diameter and countersunk. The bone screw head is then mounted in a V shaped notch cut in the driver head and a sleeve is mounted on the driver around the bone screw head and is seated on a shoulder formed by the difference in diameter of the driver head and the driver body to keep the screw head seated in the notch. The bone screw is then driven or screwed into the prepared bone bore until the undercut of the bone screw engages the countersink. The portion of the bone screw extending past the surface of the outer bone piece is then cut off so that the head of the bone screw is flush with bone piece surfaces.

These and other objects, advantages, and novel features of the present invention will become apparent when considered with the teachings contained in the detailed disclosure along with the accompanying drawings.

BRIEF DESCRIPTION OF THE DRAWINGS

FIG. 1 is a perspective view of the inventive bone fixation screw;

FIG. 2 is a reduced top plan view of the bone fixation screw shown in FIG. 1;

FIG. 3 is a side elevational view of the bone fixation screw shown in FIG. 1;

FIG. 4 is an enlarged partial elevational view of the threads of the bone fixation screw shown in Circle A of FIG. 3;

DETAILED DESCRIPTION OF PREFERRED EMBODIMENT

Figure 5:
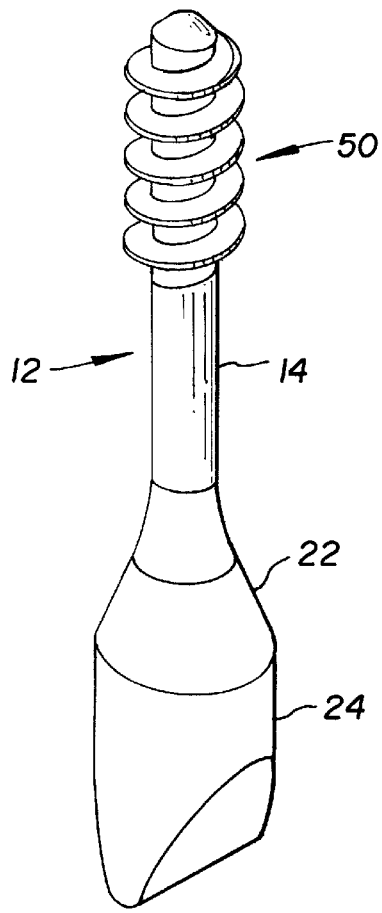
FIG. 5 is a perspective view of a variation of the inventive bone fixation screw.
Figure 6:
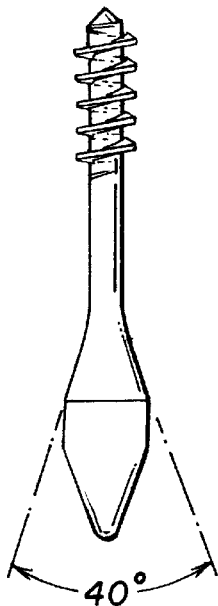
FIG. 6 is a reduced top plan view of the bone fixation screw shown in FIG. 5.
Figure 7:
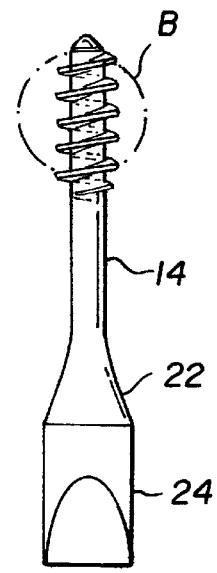
FIG. 7 is a side elevational view of the bone fixation screw shown in FIG. 6.
Figure 8:
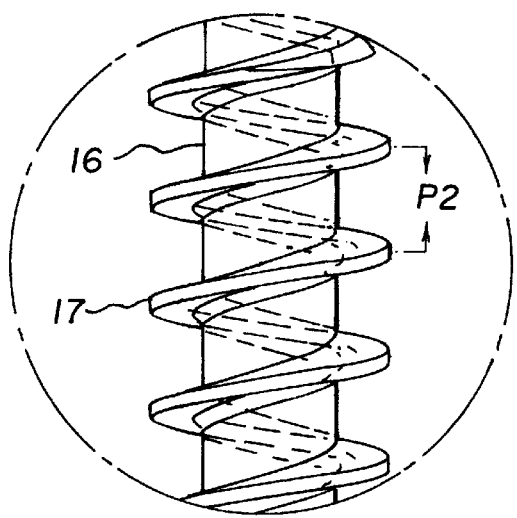
FIG. 8 is an enlarged partial elevational view of the threads of the bone fixation screw shown in Circle B of FIG. 7.
Figures 9, 10, 11:
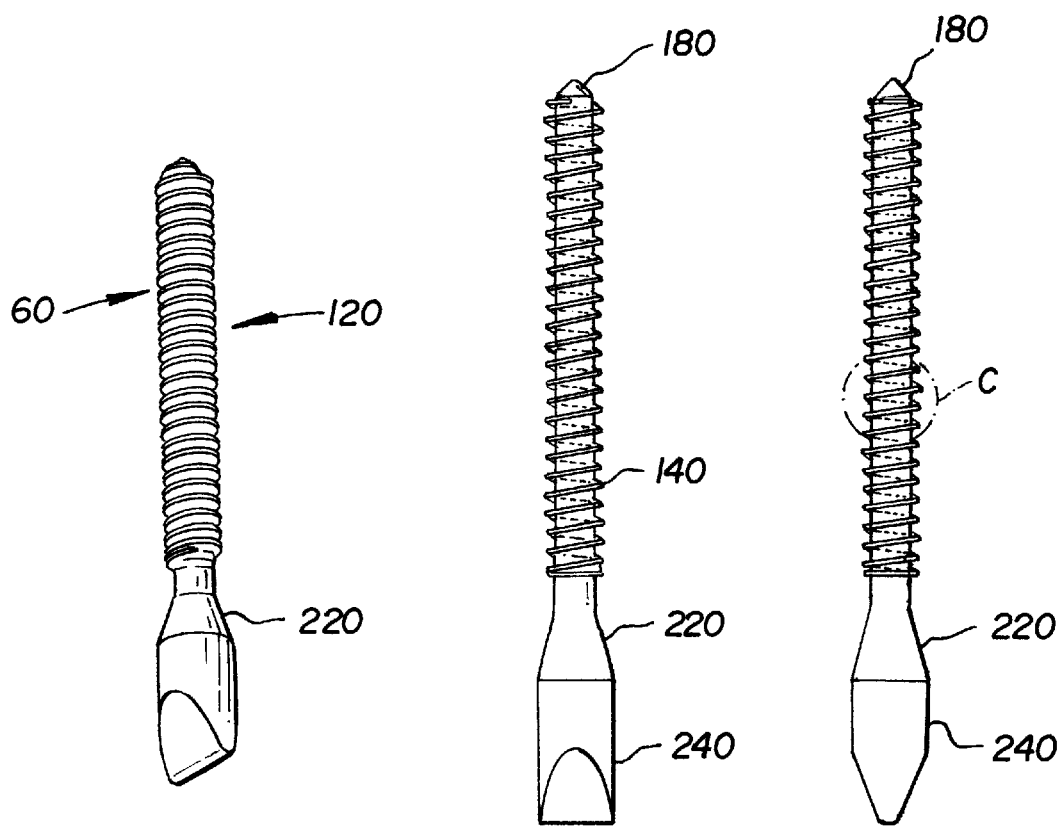
FIG. 9 is a perspective view of another embodiment of the inventive bone fixation screw.
FIG. 10 is a side elevational view of the bone fixation screw of FIG. 9.
FIG. 11 is a front elevational view of the bone fixation screw of FIG. 9.
Figure 12:
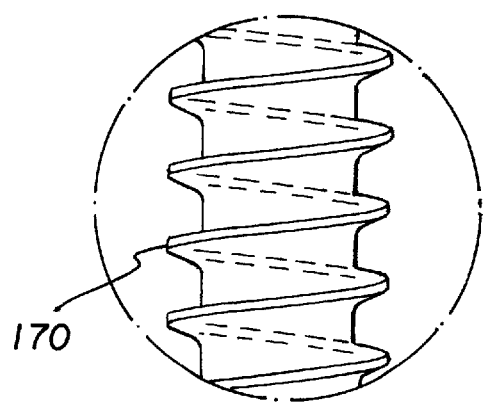
FIG. 12 is an enlarged partial elevational view of the threads of the bone fixation screw shown in Circle C of FIG. 11.

The preferred embodiment and the best mode of the present invention is shown in FIGS. 1 through 8.

It is an accepted fact that the initiation of mechanical failure in a material occurs at the outer surface of the material. Also, it is recognized that rapid changes in cross sectional geometry act as localized "stress risers", significantly increasing the risk of failure under load. The present inventive bone screw 12 solves these problems particularly when the screw is constructed of allograft bone. The preferred material is cortical allograft bone.

The bone fixation screw 12 has a shank 14 with a threaded portion 16 ending in a distal pointed tip 18 and an unthreaded portion 20 which is tapered outward at 22 ending in a wedge shaped head 24. The tapered portion 22 of the shank 14 is preferably tapered to form an angle ranging from about 30° to about 40°. The bone screw 40 used on cortical bone shown in FIGS. 1 through 4 preferably has a taper or undercut angle of about 30° and the bone screw 50 used on cancellous bone shown in FIGS. 5 through 8 preferably has a taper or undercut angle of about 40°. The overall length of the screw 12 is preferably about 35.22 mm and the shank used on cortical bone has a 3.5 mm diameter. When the shank is used on cancellous bone it will have at least a 4.0 mm diameter. The screw pitch P1 of the cortical bone screw is approximately 1.25 mm and the screw pitch P2 of the cancellous screw threads is approximately 1.75 mm. The bevel of the thread is preferably about 60°. However the included angle at the thread root can vary from 10° to 80°. It will be appreciated that these dimensions are preferred dimensions and may be varied while retaining the structure and function of the invention without limiting same. The threaded portion 16 preferably is formed with a single helical thread 17 formed on the exterior surface of the shank to engage the bone material 100 and draw the screw 12 down into the bore 102 and runs along the shank about 10 mm. The thread 17 can be a #6-32 UNC, a #6-40 UNS or BA4 (British Aircraft) thread. UNC and UNS threads have a helical generally V-shaped thread with a 60° bevel. Other screw threads which can be used are standard screw threads (ANSI): #0, #1, #2, #3, #4, #5, #6, #8, #10, #12 and ¼ inch, 5/16 inch and ⅜ inch. Metric threads M 1.6, M 2, M 2.5, M 3, M 4, M 5, M 6, M 8 and M 10 can also be used. It is also contemplated that the threaded portion 16 may include a self-tapping thread having grooves extruded along the longitudinal axis of the threads providing sharp leading edges and space for removal of osseous debris. The self-tapping aspect of the threaded portion facilitates insertion and anchoring of the screw into a patient's bone. The drive head 24 geometry embodies gradual changes in cross-sectional geometry and avoids excessive localized tensile loading on the surface of the drive geometry as will be later discussed.

Another embodiment of the bone fixation screw is shown in FIGS. 9 through 12. The bone fixation screw 120 has a substantially fully threaded shank 140 ending in a distal pointed tip 180 at one end and an unthreaded outwardly tapered portion 220 ending in a wedge shaped head 240. The tapered portion 220 of the shank 140 is preferably tapered with the cross section forming an angle ranging from 30° to 40°. The cortical bone screw 60 in FIGS. 9 through 12 preferably has an angle of around 30°. The overall length of the screw is preferably about 49.22 mm and the threaded shank has a length of about 33 mm and 3.5 mm diameter. The head 240 has a length of 9.22 mm and a diameter of about 5.0 mm. The pitch of the screw threads is approximately 1.25 mm and the bevel of the thread is preferably about 60°. However the included angle at the thread root can vary from 10° to 80°. It will be appreciated that these dimensions are preferred dimensions and may be varied while retaining the structure and function of the invention without limiting same. The threaded portion is formed with a single helical thread 170 formed on the exterior surface of the shank to engage the bone material 100 and draw the screw 120 down into the bore 102. The thread 170 can be a #6-32 UNC, a #6-40 UNS or BA4 (British Aircraft) thread. UNC and UNS threads have a helical generally V-shaped thread with a 60° bevel. Other screw threads which can be used are standard screw threads (ANSI): #0, #1, #2, #3, #4, #5, #6, #8, #10, #12 and ¼ inch, 5/16 inch and ⅜ inch. Metric threads M 1.6, M 2, M 25, M 3, M 4, M 5, M 6, M 8 and M 10 can also be used. It is also contemplated that the threaded portion may include a self-tapping thread having grooves extruded along the longitudinal axis of the threads providing sharp leading edges and space for removal of osseous debris. The self-tapping aspect of the threaded portion facilitates insertion and anchoring of the screw into a patient's bone. The drive head 240 geometry embodies gradual changes in cross-sectional geometry and avoids excessive localized tensile loading on the surface of the drive geometry.

All of the bone screws 40, 50, and 60 described above can be coated with a bone morphogenic protein to speed up bone growth and absorption into bone.

This drive geometry of the head also acts as a torque limiter due to the ability of the driver 30 to climb the incline planes 25 of the wedge shaped drive head as a desirable torque limit is reached. The intersecting inclined planes 25 of the drive head form an angle which can range between 15° and 60° but preferably form a 45° angle. The magnitude of the included angle of the drive head 24/240 geometry and the linear force applied to the drive handle 32 by the surgeon dictates the torque at which the driver 30 disengages from the head 24/240. A smaller included angle allows higher torques to be applied while a larger included angle will allow for lower torques to be applied prior to driver disengagement. Due to this ability, the design of the head can be set so that the driver 30 disengages prior to reaching torque levels that would induce mechanical failure in the head, neck, or shank of the screw.

Another unique feature of all of the fixation screws is the tapered undercut 22/220 located between the cylindrical portion of the drive head 24/240 and the threaded portion 16/140 of the screw. This tapered undercut feature accomplishes two ends. First, it acts to provide a gradual change in cross sectional geometry thus increasing the strength of the component under load and second it provides a tight engagement of the screw in the bone bore. In comparison to standard screw designs where the underside of the drive geometry sharply changes, the strength of the tapered undercut is far superior both under torque loading inherent in insertion and tensile loading post operatively.

The tapered undercut also acts as a means of securing the screw within the bone wall 100 after the drive head 24/240 has been cut flush with the bone surface. The taper allows for two means of securing fixation across the fracture or osteotomy. First, the taper feature allows for compression across the fracture site as would a conventional screw design. However, the taper also acts as a "taper lock" similar to those found in femoral head/femoral lock neck mating geometry's in Total Hip Replacement implants ensuring that even under cyclic loading conditions the screw will not "back out" of the threaded bone thus releasing the tension across the fracture or osteotomy.

Both the wedge shaped drive head 24/240 and the tapered undercut 22/220 serve to increase the strength of the screw 40, 50, 60 under torsion loading. Torsion loading induces tangential or planar shear stresses in planes normal to the longitudinal axis of the torque induced. The magnitude of these stresses is proportional to the cross section area of the material thus loaded. The shear stresses for the wedge shaped drive head are related to torque as if set forth in the following equation $$T_{max} = t_{max} J/r;$$

WHERE:

$T_{max}$ is the maximum external twisting moment (torque induced by 'driver');

$t_{max}$ is the maximum unit shear stress of the material;

J is the polar moment of inertia for the cross section;

r is the radius of the cross section.

Or in more specific terms for circular cross sections:

$$T_{max} = (\pi/2) r^3 t_{max};$$

or . . .
Equation I $$T_{max} = 1.57 \, r^3 t_{max}$$

With respect to a modified Phillips Screw driver head with two orthogonal slots the resistance to torque may be approximated as:

$$T_{max} = (txy)_v + (txy)_m$$

$(txy)_v = VQ/It$ WHERE: Q is the first moment; I is the second moment and t is the axis length (0.7r): and $(txy)_M = Tr/J_o$ WHERE: T is the twisting course m and $J_o$ is the polar moment. Substituting these components one arrives at $$T_{max} = \frac{VQ}{I(.7r)} + \frac{Tr}{J_o}$$

or . . .
Equation II $$T_{max} = 0.079 t_{max} r^3$$

Comparing the value of Equation II against Equation I, it can be readily be seen that the wedge shaped drive head 24/240 provides for a 20 fold increase in torsional loading strength with respect to a modified Phillips configuration. Such an increase in torsional loading strength is of great importance in allograft bone screws. It should be noted that no attempt has been made to include the effect of the stress riser in the Phillips type design. This factor is both geometry, material, and load rate dependent and can only serve to further reduce the strength of the Phillips style head with respect to the wedge shaped drive head. The wedge shaped drive head 24/240 and tapered undercut 22/220 of the respective screw can also be formed of other biomaterial including, but not limited to, bioceramics, biocompatible/bioresorbable polymeric materials, biocompatible carbon fiber reinforced polymer and the multitude of orthopaedic inert implant metals including stainless steel, cobalt-chromium-molybdenum alloys, titanium and titanium alloys, tantalum and niobium and their alloys, HEDROCEL, a porous tantalum-carbon composite which has a modulus of elasticity that approximates that of human bone as well as other materials used in surgical applications.

Figure 13:
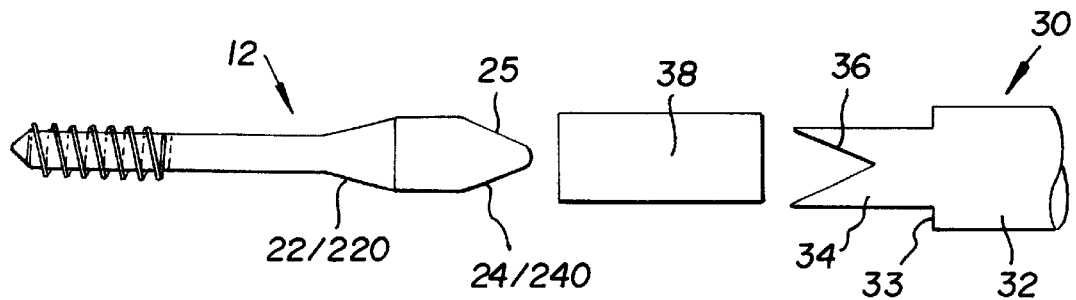
FIG. 13 is an exploded view of the bone fixation screw and driver assembly.
Figure 14:
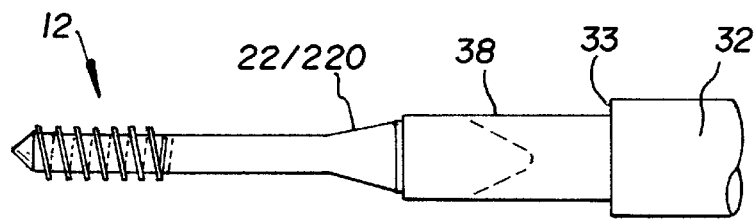
FIG. 14 is a side elevational view partially in phantom of the bone fixation screw mounted in the drive head of the drive assembly.
Figure 15:
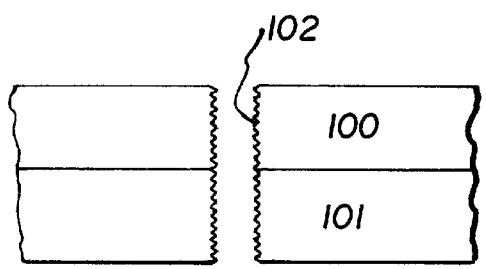
FIG. 15 is a schematic view of two adjacent bone pieces being drilled with a tapped bore.
Figure 16:
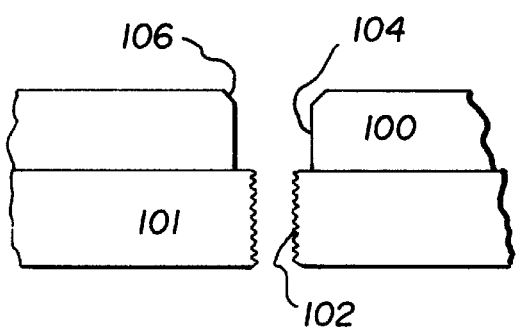
FIG. 16 is a schematic view of the bone pieces shown in FIG. 15 with the first bone piece being overdrilled with a greater diameter bore and a countersink.
Figure 17:
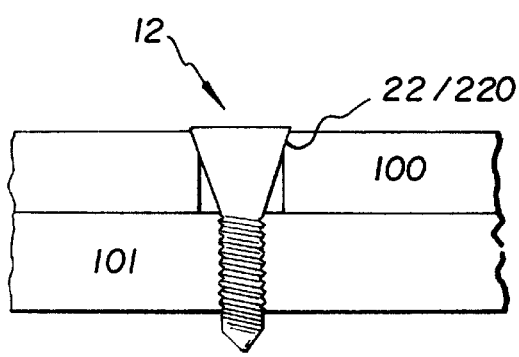
FIG. 17 is a schematic view of the bone pieces shown in FIG. 16 with the bone fixation screw mounted in the bone pieces and the screw head severed flush to the bone surface.

The use of the implant driver 30 is shown with reference to FIGS. 13 and 14. The cylindrical shaft body 32 of the driver is formed with a cylindrical head 34 having a lesser diameter than shaft body 32 forming shoulder 33. The head 34 defines an angular "V" shaped notch or recess 36 at its distal end preferably of 45° or any other suitable angle which engages and seats the wedge shaped head 24/240 of the bone screw therein and applies a suitable amount of torque to the screw. A sleeve 38 having an inner diameter greater than the outer diameter of the head 34 but less than outer diameter of shaft 32 is seated on a shoulder 33 and holds screw head 24/240 within notch 36.

In seating the screw, a threaded bore 102 is drilled through both bone portions 100 and 101, with portion 100 being over drilled with a larger diameter bore 104 having a countersink 106 of a tapered geometry which widens from the diameter of the bore at the same angle as tapered portion 22/220. The bore can be cut in a single stage or two stage operation in which the countersink is initially cut into the bone in the second cut or followed by a third cut. In the single stage cut, a drill (not shown) is provided with a drill bit with a widened tapered portion which enables drilling a bore with a tapered end section geometry which is of the same size and configuration as the undercut 22/220 of screw. A bone screw comprising a shank with a uniform diameter threaded portion, and a driving head 24/240 with a substantially wedge shaped end portion is seated in the wedge shaped notch seat 36 in the driver member head 34. The driver member is preferably constructed of steel and comprises a cylindrical shaft body 32, a cylindrical driver head 34 secured or integrally formed with the shaft body forming a shoulder 33 with the shaft body. A sleeve collar 38 is mounted around the driver head 34 engaging and seated on the shoulder 33. The screw is driven into the previously drilled stepped bore 102/104 until the tapered portion or countersink 106 of the bore creates a mating surface for the tapered undercut 22/220 of the bone screw. The cylindrical portion of the head allows the driver head 34 to be raised above the bone surface being repaired providing clearance for the driver. The head 24/240 is then cut off flush to the bone surface.

In the foregoing description, the invention has been described with reference to a particular preferred embodiment, although it is to be understood that specific details shown are merely illustrative, and the invention may be carried out in other ways without departing from the true spirit and scope of the following claims:

What we claim is:

1. A bone screw constructed of cortical allograft bone comprising a shank with a threaded portion and an unthreaded portion which tapers outwardly adjacent an integrally formed drive head to form a tapered undercut for the drive head, said tapered undercut being funnel shaped and tapered at an angle of about 40° when viewed in cross section, said drive head defining a wedge shaped end.

2. A bone screw as claimed in claim 1 wherein said bone screw shank has at least a 4.0 mm diameter.

3. A bone screw as claimed in claim 1 wherein said screw is threaded for about ⅓ the length of the screw.

4. A bone screw as claimed in claim 1 wherein the wedge shaped drive head has a shear stress in relation to torque determined by the formula $T_{max}=1.57\ r^3 t_{max}$.

5. A bone screw as claimed in claim 1 wherein said threaded shank portion has screw threads with a pitch of about 1.75 mm.

6. A bone screw as claimed in claim 1 wherein said allograft bone is coated with a bone morphogenic protein.

7. A bone screw constructed of cortical allograft bone comprising a shank with a threaded portion and an unthreaded portion which tapers outwardly adjacent an integrally formed drive head to form a tapered undercut for the drive head, said tapered undercut being funnel shaped and tapered at an angle of about 30° when viewed in cross section, said drive head defining a wedge shaped end.

8. A bone screw as claimed in claim 1 wherein said bone screw shank has about a 3.5 mm diameter.

9. A bone screw as claimed in claim 1 wherein said screw is threaded for about ⅓ the length of the screw.

10. A bone screw as claimed in claim 1 wherein the wedge shaped drive head has a shear stress in relation to torque determined by the formula $T_{max}=1.57\ r^3 t_{max}$.

11. A bone screw as claimed in claim 1 wherein said threaded shank portion has screw threads with a pitch of about 1.25 mm.

12. A bone screw as claimed in claim 1 wherein said allograft bone is treated with a bone morphogenic protein.

13. A bone screw as claimed in claim 1 wherein said allograft bone screw is impregnated with a biological agent facilitating fixation, ingrowth or resorption.

14. A bone screw constructed of allograft bone comprising: a shank provided with a thread of a given pitch running along substantially its entire length and terminating at an unthreaded outwardly flaring conical section having a diameter which is greater than the diameter of said threaded portion, said conical section being adjacent to and integrally formed with a wedge shape drive head with angular inclined planes, said outwardly flaring conical section forming a tapered undercut for said drive head.

15. A bone screw as claimed in claim 14 wherein said allograft bone is cancellous bone.

16. A bone screw as claimed in claim 14 wherein the wedge shaped drive head has a shear stress in relation to torque calculated by the formula $T_{max}=1.57\ r^3 t_{max}$.

17. A bone screw as claimed in claim 14 wherein said threaded shank portion has screw threads with a pitch ranging from about 1.25 mm to about 1.75 mm.

18. A bone screw as claimed in claim 14 wherein said is allograft bone is cortical bone.

19. A bone screw as claimed in claim 14 wherein said allograft bone screw is coated with a bone morphogenic protein.

20. A bone screw as claimed in claim 14 wherein said tapered undercut forms an angle ranging from about 30° to about 40°.

21. A method of mounting a bone screw in a two adjacent pieces of bone comprising the steps of:
   a) drilling a threaded bore in both pieces of bone;
   b) overdrilling the bore in one piece of bone to form a wider diameter stepped bore so that the threaded portion of a bone screw can easily pass therethrough;
   c) top drilling the overdrilled bore to form a countersink;
   d) placing a bone screw comprising a shank with a threaded portion and an integrally formed driving head defining a tapered undercut into the stepped bore until the threaded portion engages the threaded bore;
   e) rotating said screw in said stepped cut bore until the tapered surface of the bore engages the tapered undercut of the screw; and
   f) cutting off a portion of the head of the screw so that the head portion is substantially flush with the surface of a bone piece.

22. A method of mounting a bone screw as claimed in claim 21 wherein said bone screw is constructed of allograft bone.

23. A method of mounting a bone screw as claimed in claim 21 wherein said steps of drilling an overdrill bore and countersink in the bone are combined.

* * * * *